United States Patent
Karpinski (10) Patent No.: US 7,897,935 B2
(45) Date of Patent: Mar. 1, 2011

(54) RADIOPHARMACEUTICAL PURIFICATION

(75) Inventor: Krysztof Karpinski, Yarra Glen (AU)

(73) Assignee: Quark Technologies Australia Pty Ltd., Victoria (AU)

( * ) Notice: Subject to any disclaimer, the term of this patent is extended or adjusted under 35 U.S.C. 154(b) by 253 days.

(21) Appl. No.: 12/267,358

(22) Filed: Nov. 7, 2008

(65) Prior Publication Data
US 2010/0108906 A1 May 6, 2010

(30) Foreign Application Priority Data
Nov. 6, 2008 (AU) ............................... 2008243144

(51) Int. Cl.
G01N 23/10 (2006.01)
G21F 5/00 (2006.01)
(52) U.S. Cl. .......... 250/436; 250/506.1; 435/4; 435/183
(58) Field of Classification Search .................. 250/428, 250/436, 505.1, 506.1; 435/4, 6, 183
See application file for complete search history.

(56) References Cited

U.S. PATENT DOCUMENTS

| | | | | |
|---|---|---|---|---|
| 5,591,581 A | * | 1/1997 | Massey et al. | 435/6 |
| 5,716,781 A | * | 2/1998 | Massey et al. | 435/6 |
| 5,811,236 A | * | 9/1998 | Massey et al. | 435/6 |
| 6,316,607 B1 | * | 11/2001 | Massey et al. | 536/22.1 |
| 6,468,741 B1 | * | 10/2002 | Massey et al. | 435/6 |
| 6,500,609 B1 | * | 12/2002 | Ribeill et al. | 506/3 |
| 6,916,606 B2 | * | 7/2005 | Massey et al. | 435/5 |
| 7,704,990 B2 | * | 4/2010 | Landry et al. | 514/211.05 |
| 2003/0148291 A1 | * | 8/2003 | Robotti | 435/6 |
| 2004/0224918 A1 | * | 11/2004 | Yatvin et al. | 514/47 |
| 2006/0194767 A1 | * | 8/2006 | Marks et al. | 514/81 |
| 2007/0049572 A1 | * | 3/2007 | Marks et al. | 514/211.09 |
| 2007/0066851 A1 | * | 3/2007 | Liu et al. | 568/349 |
| 2007/0173482 A1 | * | 7/2007 | Marks et al. | 514/80 |

* cited by examiner

Primary Examiner — Bernard E Souw
(74) Attorney, Agent, or Firm — Patterson, Thuente, Christensen, Pederson PA (57) ABSTRACT

An improved method and apparatus for radiopharmaceutical purification, the apparatus including a chromatographic separating device, a UV-absorption detector, a radioactivity detector and a collection container having a collection inlet valve located at a collection location. Propagation times of eluent between the UV-absorption detector and the radiation detector, as well as between one or both of the detectors and the collection inlet valve, are determined. UV-absorption and radiation data from the detectors are monitored, and an appropriate time period during which the collection valve should be opened is established. Preferably, monitoring and operation of the apparatus is under control of a computer. A user interface display may be provided to enable an operator to monitor the purification process, and to intervene as required and/or appropriate.

11 Claims, 8 Drawing Sheets

RADIOPHARMACEUTICAL PURIFICATION

CLAIM TO FOREIGN PRIORITY

This Application claims foreign priority to Australian Patent Application No. 2008243144, entitled "IMPROVEMENTS IN RADIOPHARMACEUTICAL PURIFICATION," and having a filing date of Nov. 6, 2008.

FIELD OF THE INVENTION

The present invention generally relates to the production of radiopharmaceuticals, and more particularly to improved methods and apparatus for the purification of the products of radiopharmaceutical synthesis.

BACKGROUND OF THE INVENTION

Radioactive compositions have a range of diagnostic and therapeutic applications. However, the half-life of radiopharmaceuticals is typically on the order of hours, and it is therefore not possible to retain stocks of such compounds within hospitals, clinics and/or research laboratories. Rather, it is necessary to synthesise and purify radiopharmaceuticals on-demand, for example within a hospital or clinical laboratory. Purification is often achieved via chromatographic techniques, such as high-performance liquid chromatography (HPLC), which perform temporal and spatial separation of the desired product from attendant impurities and by-products.

Such methods of purification carry an associated risk of the product including impurities, for example if collection is commenced too early, or concluded too late. It is undesirable, and potentially highly detrimental, for impurities or by-products of radiopharmaceutical synthesis to be injected into the patient or subject.

The operator of the synthesis and purification apparatus may therefore adopt a conservative approach, for example collecting only a portion of the desired product by commencing collection later than necessary and/or halting collection earlier than necessary. This results in a reduced volume of the desired radiopharmaceutical product, with an associated risk that an insufficient activity of the desired product will be collected.

SUMMARY OF THE INVENTION

One aspect of the invention has been developed to, at least in part, provide an improved automated method and apparatus enabling mitigation of the uncertainties and risks inherent in existing approaches to radiopharmaceutical purification.

More particularly, aspects of the invention may be applied in an apparatus for purifying the product of a reaction to synthesise a radiopharmaceutical compound, wherein the apparatus includes a chromatographic separating device, such as an HPLC column, a UV-absorption detector located at a UV-monitoring location, a radioactivity detector, such as a scintillation counter, located at a radioactivity monitoring location, and a collection container having a collection inlet valve located at a collection location. The separating device, the UV-absorption detector, the radiation detector, and the collection valve are interconnected via suitable tubing to permit flow of eluent therebetween.

In one aspect, the invention provides a method of collecting the purified radiopharmaceutical compound which comprises the steps of:

determining a first eluent propagation time between the UV-monitoring location and the radiation-monitoring location;

determining a second eluent propagation time from at least one of the UV-monitoring location and the radioactivity-monitoring location to the collection location;

passing the synthesis product through the chromatographic separating device to produce a corresponding eluent;

monitoring UV absorption of the eluent to identify a first time period in which a substantially pure sample of the radiopharmaceutical compound is present at the UV-monitoring location;

monitoring radioactivity of the eluent to identify a second time period in which a substantially high concentration of the radiopharmaceutical compound is present at the radioactivity-monitoring location;

determining a third time period in which a substantially pure sample of the radiopharmaceutical compound is present at the collection location in a substantially high concentration, based upon said first time period, said second time period, said first eluent-propagation delay, and said second eluent-propagation delay; and opening the collection inlet valve during the third time period to collect the purified radiopharmaceutical compound in the collection container.

It will be appreciated that, in the context of the invention, the term "substantially pure" refers to the sample having sufficient purity for the intended application, typically injection into a patient or other subject. The criteria may therefore vary, depending upon the particular radiopharmaceutical compound and synthesis process, however in any given case it would be possible to specify a suitable threshold of UV absorption, measured at the UV-monitoring location, corresponding with the presence of the desired radiopharmaceutical compound in a sufficiently pure form.

Similarly, the term "substantially high concentration", in the context of the invention, means a sufficient concentration for the intended purpose of collection. Due to the correlation between concentration and radioactivity levels, in any given case it would be possible to establish an appropriate threshold of radioactivity at the radioactivity-monitoring location corresponding with the required concentration.

In another aspect of the invention, the purifying apparatus comprises:

means for determining a first eluent-propagation time between the UV-monitoring location and the radiation-monitoring location;

means for determining a second eluent-propagation time from at least one of the UV-monitoring location and the radiation-monitoring location to the collection location;

means for monitoring the UV absorption of the eluent to identify a first time period in which a substantially pure sample of the radiopharmaceutical compound is present at the UV-monitoring location;

means for monitoring radioactivity of the eluent to identify a second time period in which a substantially high concentration of the radiopharmaceutical compound is present at the radioactivity-monitoring location;

means for determining a third time period in which a substantially pure sample of the radiopharmaceutical compound is present at the collection location in a substantially high concentration, based upon said first time period, said second time period, said first eluent-propagation delay, and said second eluent-propagation delay; and means for opening the collection inlet valve during the third time period to collect the purified radiopharmaceutical compound in the collection container.

In preferred embodiments, the apparatus comprises:

at least one microprocessor;

at least one memory device operatively associated with the microprocessor;

at least one peripheral interface operatively associated with the microprocessor and enabling the microprocessor to receive UV-absorption data from the UV-absorption detector and radioactivity data from the radioactivity detector, wherein the memory device comprises computer-executable instruction code stored therein which, when executed by the microprocessor, causes the microprocessor to execute the steps of:

determining a first eluent-propagation time between the UV-monitoring location and the radiation-monitoring location;

determining a second eluent-propagation time from at least one of the UV-monitoring location and the radiation-monitoring location to the collection location;

receiving UV-absorption data from the UV-absorption detector in order to identify a first time period in which a sample of the radiopharmaceutical compound is present at the UV-monitoring location;

receiving radioactivity data from the radioactivity detector so as to identify a second time period in which a substantially high concentration of the radiopharmaceutical compound is present at the radioactivity-monitoring location;

determining a third time period in which a substantially pure sample of the radiopharmaceutical compound is present at the collection location in a substantially high concentration, based upon said first time period, said second time period, said first eluent-propagation delay, and said second eluent-propagation delay; and generating an indication, during said third time period, that the collection inlet valve should be opened in order to collect the purified radiopharmaceutical compound in the collection container.

In some embodiments, the collection inlet valve may include an electrical control input for opening and closing the valve, and the apparatus may include means, such as a suitable peripheral interface between the microprocessor and the valve-control input, enabling the collection inlet valve to be opened during the third time period under automated control, in response to the generated indication. Alternatively, or additionally, the apparatus may include a display, and a visual indication may be generated on the display during the third time period enabling the operator of the apparatus to open the collection inlet valve under manual control.

Further preferred features and advantages of the invention will be apparent to those skilled in the art from the following description of a preferred embodiment of the invention, which should not be considered to be limiting of the scope of the invention as defined in the preceding statements, or in the claims appended hereto.

BRIEF DESCRIPTION OF THE DRAWINGS

A preferred embodiment of the invention is described with reference to the accompanying drawings, in which like reference numerals refer to like features, and wherein:

FIGS. 5, 6, 7, 8 and 9 are screenshots illustrating a user interface of a computer-controlled apparatus according to an embodiment of the invention, wherein more specifically.

DETAILED DESCRIPTION OF THE PREFERRED EMBODIMENTS

Figure 1:
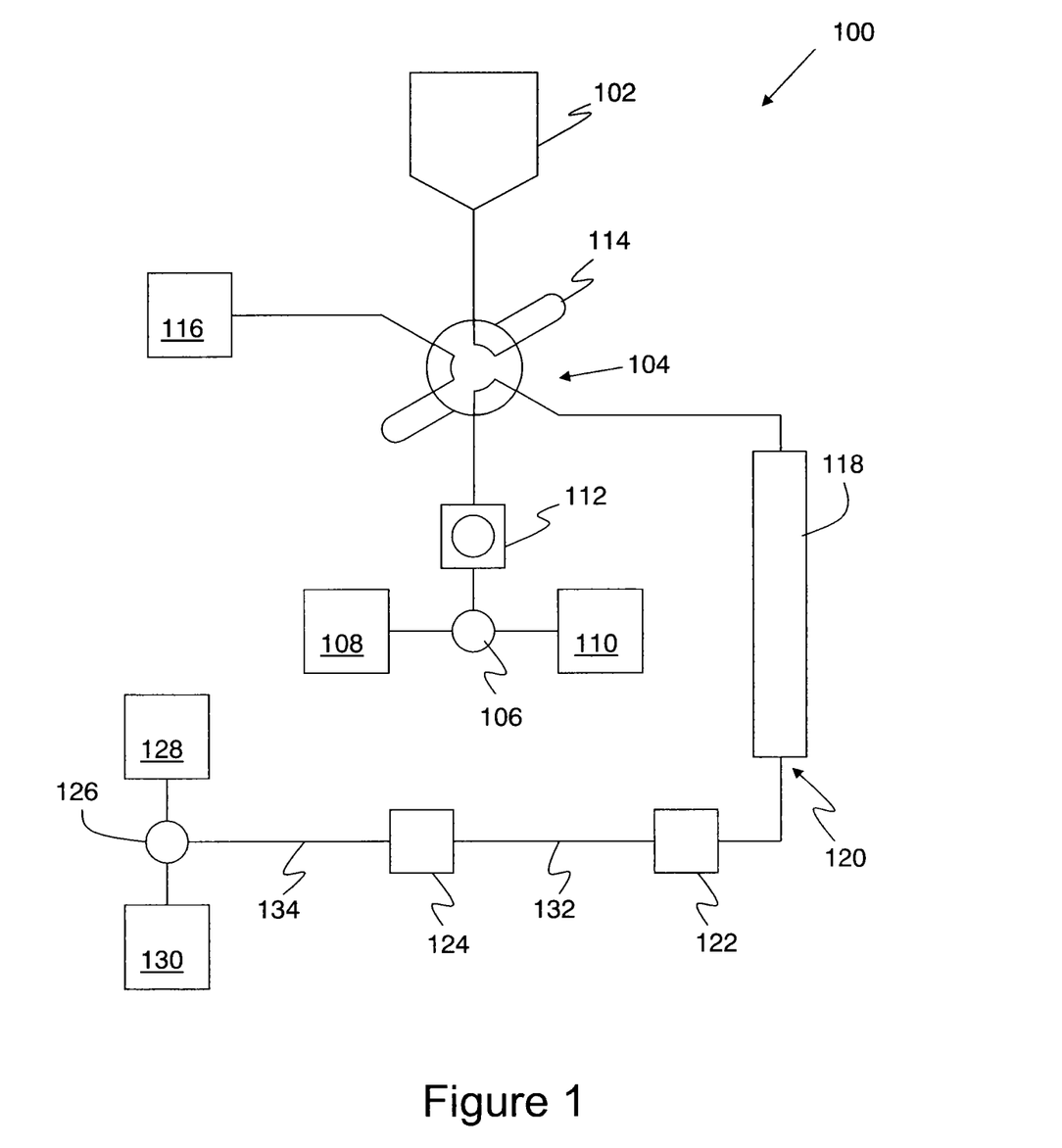
FIG. 1 is a schematic diagram illustrating elements of a system for purifying the product of a radiopharmaceutical synthesis reaction, according to an embodiment of the invention.

FIG. 1 illustrates schematically the major elements of a system for purifying the product of a radiopharmaceutical synthesis reaction, according to a preferred embodiment of the invention.

In particular, the system 100 includes an input 102, via which raw synthesis products are received. Details of the synthesis process will depend upon specifics of a radiopharmaceutical product that is to be obtained, and are not relevant to the present invention. For present purposes, it is sufficient to note that the raw synthesis product includes the desired radiopharmaceutical compound, along with undesired impurities and by-products. In accordance with embodiments of the invention, the desired radiopharmaceutical compound is temporally and spatially separable from the undesired components via chromatographic techniques, such as HPLC.

A six-way rotary valve 104 facilitates communication of fluids between various elements of the system 100, as described in greater detail below.

In one part of the system 100, a valve 106 provides for selection between a mobile phase solution 108 and a rinse solvent 110. The valve 106 communicates the selected liquid to a pump 112, which is used to drive the separation process, as described in greater detail below. The pump 112 is connected to a port of the six-way valve 104.

A sample storage loop 114, consisting of a suitable length of tubing, is connected between two further ports of the six-way valve 104. Another port of the valve 104 is connected to a waste storage container 116. The final port of the valve 104 is connected to one or more chromatographic separating columns, such as HPLC column 118. While the system 100 includes only one separating column 118, where multiple columns are provided an additional column selection valve may also be included.

When the raw synthesis product is available for purification, the rotary valve 104 is configured to allow the raw product to enter the storage loop 114. Preferably, the storage loop 114 is of an appropriate length to contain the exact volume of raw product available. However, any excess is directed to the waste storage container 116.

Prior to and/or during this period, the valve 106 may be used to select the rinse solvent 110, and the pump 112 operates to drive the rinse solvent through the HPLC column 118, and the rest of the purification system, in preparation for the purification process. As will be appreciated, rinsing is optional, and may be performed before and/or after purification, depending upon requirements. Prior to purification, however, the valve 106 should be operated in order to select the mobile phase solution 108, which is then allowed to fill the system prior to commencement of purification.

Once the storage loop 114 is full, the six-way rotary valve 104 is operated such that the pump 112 drives the raw synthesis products into the HPLC column 118. Within the column 118, chromatographic separation of the component parts of the raw synthesis products occurs, and the resulting eluent emerges at the column output 120. The eluent passes, via suitable tubing, through a UV-absorption detector 122, a radiation detector, such as a scintillation counter 124, and via a further valve 126, to either a waste container 128, or a radiopharmaceutical product container 130.

The valve 126 is a collection valve, which is operated at the appropriate time in order to direct the desired purified radiopharmaceutical product into the collection container 130, on the basis of UV absorption and radioactivity measurements acquired from the detectors 122, 124.

The UV-absorption detector 122 and the radiation detector 124 provide information that may be used to identify the presence of the desired radiopharmaceutical compounds within the eluent output from the HPLC column 118. This information may therefore be used to direct the operation of the collection valve 126, as described in greater detail below.

Turning firstly to the UV-absorption detector 122, this device typically comprises a UV light source and a corresponding detector, wherein the path of the eluent passes between the source and the detector. The output frequency or spectrum of the UV source may be selectable, or controllable, in accordance with the contents of the eluent. For example, by selection of an appropriate wavelength of UV light, the corresponding absorption of the desired radiopharmaceutical compound may be substantially lower than the absorption of undesired impurities and by-products in the eluent, such that the presence of the desired compound corresponds with an increase in UV energy received at the UV detector. Accordingly, as the purity of the radiopharmaceutical compound increases, an increase in the detected signal, photocurrent or corresponding voltage, will be observed. Collection of the radiopharmaceutical compound should be timed to coincide with the passage of a portion of the eluent for which the UV-absorption readings indicate a substantially pure sample of the desired radiopharmaceutical compound.

Furthermore, readings obtained using the radioactivity detector 124 are correlated with the concentration of the radiopharmaceutical compound passing through the detector. At higher levels of concentration, greater radioactivity will be detected, in the form of an output current, or corresponding voltage of the detector 124.

Significantly, the eluent passes from the UV detector 122 to the radiation detector 124 via a length of feed line or tubing 132, and from the radiation detector 124 to the collection valve 126 via a further length of feed line or tubing 134. Accurate determination of the appropriate time for collection of the purified radiopharmaceutical product by operation of the collection valve 126 is complicated by the fact that the propagation delay of eluent passing through the lengths of tubing 132, 134 is dependent upon the particular setup of the purification apparatus, and the fact that these delays may be significant compared to the relevant collection period.

Figure 2:
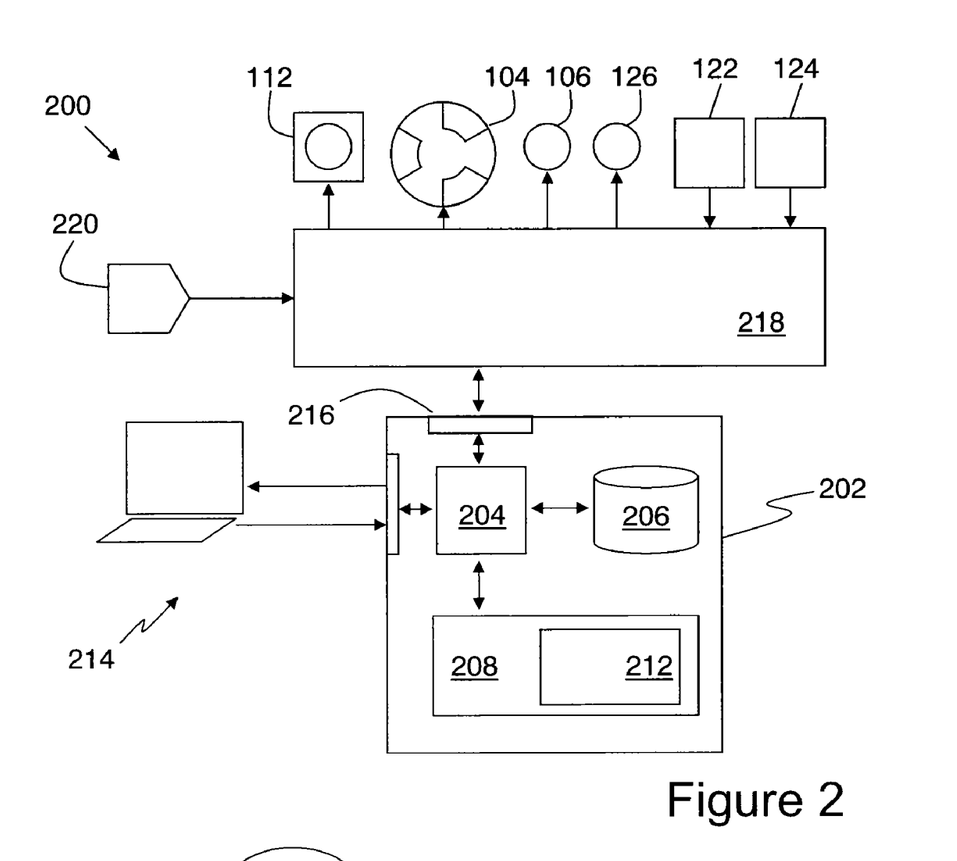
FIG. 2 is a schematic diagram illustrating a microprocessor based apparatus for monitoring and/or controlling a process of purification of the product of a radiopharmaceutical synthesis reaction, according to an embodiment of the invention.

FIG. 2 is a schematic diagram illustrating a microprocessor-based apparatus 200 for monitoring and/or controlling the process of purification of the desired radiopharmaceutical product, using the system 100 illustrated in FIG. 1. The exemplary apparatus 200 includes a computer 202 having at least one microprocessor 204, which is interfaced, or otherwise associated, with a high-capacity, non-volatile memory/storage device 206, such as one or more hard-disk drives. The storage device 206 is used for permanent or semi-permanent storage of program instructions and data relating to the operation of the computer 202, and the implementation of the preferred embodiment of the present invention.

The computer 202 further includes an additional storage medium 208, typically being a suitable type of volatile memory, such as random access memory, for containing executable program instructions and transient data relating to the operation of the computer 202. In particular, the memory device 208 contains a body of program instructions 212 implementing various software-implemented features of the present invention, as described in greater detail below, with reference to the remaining drawings. In general, these features include analysis and processing functions, such as for receiving data from various components of the system 100, and for controlling various other components of the system 100, as well as for interacting with an operator of the apparatus 200 via a suitable user interface.

To facilitate operation of the apparatus 200, the computer 202 has associated input/output devices 214, such as a display monitor, keyboard and/or suitable pointing device (ie a mouse).

A further peripheral interface 216 which may be a custom interface, or a standard interface such as an RS-232 and/or USB serial port. The peripheral interface 216 is used to connect the computer 202 to a data acquisition and control circuit 218. In an exemplary embodiment the data acquisition and control card 218 is a commercially-available National Instruments NI DAQPad-6015 Multifunction Data Acquisition and Control Card. This particular device is interfaced to a conventional PC via a USB port, and includes 16 analog inputs, eight digital input/output ports, two analog outputs, and two counter/timers. Associated driver software is available for installation on the PC, and is compatible with National Instruments LabVIEW software, as well as Measurement Studio for Visual Studio .NET, and other programming environments. However, the invention is not limited to this particular hardware and software, and in other embodiments alternative data acquisition and control hardware may be employed, including custom hardware designed and constructed using suitable analog and digital electronic components.

In accordance with the exemplary apparatus 200, the data acquisition and control card 218 is interfaced to a number of devices within the system 100. An input signal 220 may be provided by the synthesiser (not shown), indicating when the synthesised raw product is available at the input 102. This signal may be acquired and used to initiate the purification process, either under automated control, or manual control. In the latter case, the presence of the signal 220 may be used to trigger a visual indication via the user interface devices 214, informing the operator that the synthesised product is available for purification.

The data acquisition and control card 218 is configured to provide output signals controlling the pump 112, the six-way rotary valve 104, the selection valve 106, and the collection valve 126. In embodiments having multiple separating columns, a column selection valve may also be provided that is able to be controlled via the data acquisition and control card 218. Inputs, for example analog voltage inputs, are received from the UV-absorption detector 122 and the radiation detector 124, which are converted into digital form on board the data acquisition and control card 218, whereby they are made available via the peripheral interface 216 for processing by the microprocessor 204 under control of program instructions 212. In general, the entire system 100 may be relevantly monitored and controlled from the microprocessor 204 via the data acquisition and control card 218, and such monitoring and control is limited only by the input and output interfaces provided by the various devices utilised within the system 100. Accordingly, embodiments of the invention that are more or less sophisticated in their degree of automation, monitoring and control, as compared with the presently preferred embodiment, may readily be implemented by appropriate selection of components, and corresponding programming.

Figure 3:
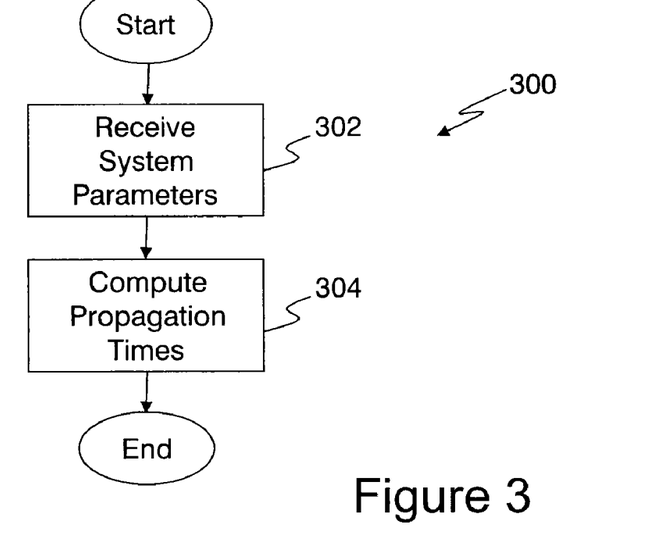
FIG. 3 is a flowchart illustrating propagation time calculation according to an embodiment of the invention.
Figure 4:
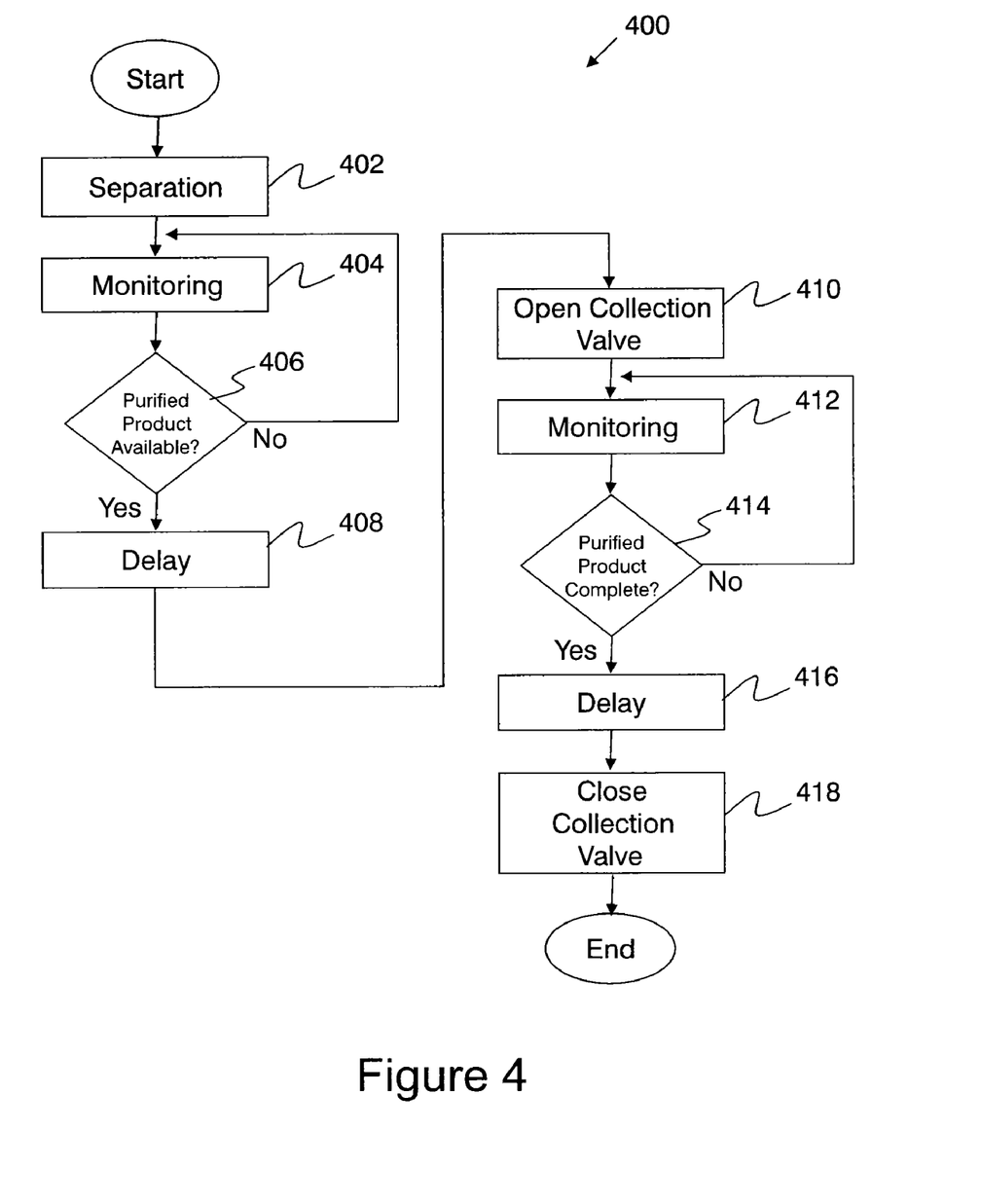
FIG. 4 is a flowchart illustrating a process of collection of purified radiopharmaceutical product, according to an embodiment of the invention.

The discussion will now turn to the algorithms implemented within the apparatus 200, with reference to FIGS. 3 and 4. In particular, FIG. 3 is a flowchart 300 which illustrates system configuration and propagation time calculation in accordance with the preferred embodiment of the invention, whereas FIG. 4 is a flowchart 400 illustrating the process of collection of purified products.

The system 100 has a number of parameters that are relevant to the purification process. For the purpose of describing the preferred embodiment, the relevant parameters include, without limitation, the pumping rate of the pump 112, as well as the respective interior diameters and lengths of the connecting tubes 132 and 134. For ease of reference, the diameter and length of tube 132 are hereafter denoted $D_1$ and $L_1$, whereas the diameter and length of tube 134 are denoted $D_2$ and $L_2$. The pumping rate of the pump 112 is denoted by Q, and may be measured in units such as mm³/s or ml/min. Lengths and diameters are conveniently represented in millimeters.

In some embodiments of the invention, the pumping rate of the pump may be electronically controllable, and therefore subject to total control via the computer 202. In other embodiments, such as the presently preferred embodiment described herein, the pumping rate of the pump 112 is fixed, or manually selectable, and the relevant pumping rate is then preferably input to the computer 202 via the user interface devices 214. Similarly, the relevant dimensions of the tubes 132, 134 may be provided by the operator via the input devices 214. For example, the internal diameter of the tubes 132, 134 will generally be a known property of the type of tubing employed, and the relevant lengths may be measured, and this data manually entered into the computer 202. Alternatively, one or more standard configurations of tubing may be provided, each having an associated standard identifier, whereby entry of the relevant identifier into the computer 202 fully specifies the relevant diameters and lengths. In still further embodiments, various components of the system 100 may be provided as preassembled installable cartridges, and markings or other features of the cartridges, that may be either manually or computer-readable, may be used to indicate the relevant dimensions of the tubes 132, 134.

Accordingly, as shown in the flowchart 300, at step 302, the computer receives relevant parameters of the system 100 either via the input devices 214, or directly by interrogation and/or control of the relevant components via the data acquisition and control card 218.

Subsequently, at step 304, the computer is programmed to calculate relevant propagation times of the eluent through the tubes 132, 134. In particular, the propagation time T for eluent passing through a tube of the internal diameter D, and of length L, is given by the following equation:

$$T = \pi \frac{D^2 L}{4Q}$$

By way of example, for a typical flow rate of 4 ml/min, and for ID tubing having a 1/32" inner diameter, the propagation delay is around 7.5 s/m. Using the received system parameters, a first eluent propagation time between the UV-monitoring location and the radiation-monitoring location, $T_1$, and a second eluent propagation time between the radioactivity monitoring location and the collection location, $T_2$, are calculated as follows:

$$T_1 = \pi \frac{D_1^2 L_1}{4Q}$$

$$T_2 = \pi \frac{D_2^2 L_2}{4Q}$$

It will be appreciated that, depending upon the system setup, and specific design choices and requirements, an alternative, but equivalent, pair of propagation delays may be calculated. For example, the radiation detector 124 may be placed prior to the UV-absorption detector 122 within the path of flow of the eluent, in which case corresponding adjustments may be made in the definitions of the calculated propagation delays. Furthermore, an alternative definition of the relevant second eluent propagation time could be based upon the total propagation time from the first (ie UV-absorption) detector 122 to the collection valve 126, and its alternative delay would be equal to the sum of $T_1$ and $T_2$ computed above. All such readily-implemented variations fall within the scope of the present invention.

Once the system parameters have been received, and relevant propagation times calculated, purification and collection of the desired radiopharmaceutical compound may commence, in accordance with the flowchart 400. In particular, at step 402 separation commences, as previously described, by operation of the six-way rotary valve to inject the raw product into the HPLC column 118. Step 404 represents a monitoring of the UV-absorption and radioactivity of the eluent output 120 via the detectors 122, 124. Processing of the data received from the detectors 122, 124 enables a decision 406 to be made, regarding whether purified compound is available. If not, then monitoring continues. However, if the desired radiopharmaceutical compound is determined to be present in a sufficiently pure form, after an appropriate delay 408, to allow the pharmaceutical compound to reach the collection valve 126, the valve is opened at step 410.

Collection of the radiopharmaceutical compound within the collection container 130 then commences, while the computer 202 continues to monitor the detectors 122, 124, as indicated at step 412. Processing of the data received from the detectors 122, 124 enables a determination as to whether passage of the purified radiopharmaceutical compound is complete, as indicated via decision step 414. If not, then monitoring continues. However, when it is determined that passage of the sufficiently pure desired compound is complete, an appropriate delay is allowed to pass, at step 416, while collection is completed, and then the collection valve 126 is closed at step 418.

Suitable criteria and algorithms for determining the presence of sufficiently pure radiopharmaceutical compound, and corresponding control of the collection valve 126, will now be described.

Specifically, the collection valve 126 is opened, and collection continued, during a time period which depends upon a first time period during which data received from the UV detector indicates the presence of a sufficiently pure sample of the radiopharmaceutical compound, and a second time period during which data received from the radioactivity detector indicates that a sufficiently high concentration of the radiopharmaceutical compound is present. The collection period depends upon these first and second time periods, as well as the propagation delays $T_1$ and $T_2$. It is accordingly a requirement to define suitable criteria for determining the commencement and duration of the relevant time periods.

In general terms, a first criterion or trigger may be defined in relation to the data received from the first detector in the purification system 100, while a second criterion or trigger may be defined in relation to the data received from the second detector. When both of these criteria, conveniently denoted $C_1$ and $C_2$, are simultaneously satisfied, then collection of the purified radiopharmaceutical compound is indicated. It will be appreciated that in the system 100, in which the UV detector 122 precedes the radioactivity detector 124, the criterion $C_1$ is associated with the purity of the product assessed via UV-absorption at the detector 122, while the criterion $C_2$ is associated with levels of radioactivity detected at the detector 124. For simplicity, the following analysis is based upon the embodiment 100, although it will be appreciated that the order of the detectors 122, 124 may be reversed in alternative embodiments, with corresponding changes made as required to the analysis.

In order to maximize yield, and avoid the collection of insufficiently pure product, proper account must be taken of the delays in the tubes 132, 134. It is convenient to define the collection criteria as boolean functions of time $C_1(t)$, $C_2(t)$. Each of these functions is "true" at times when the relevant criteria are satisfied, and "false" otherwise. Defining a function $T(C)$ to be the time at which the condition (C) becomes true, it is possible to define a collection start time $T_{start}$ and a collection stop time $T_{stop}$ in the following manner:

$$T_{start} = T(C_1(t-T_1) \text{ AND } C_2(t)) + T_2$$

$$T_{stop} = T(\overline{C_1(t-T_1) \text{AND} C_2(t)}) + T_2$$

$$T_{stop} > T_{start}$$

It will be appreciated that the above equations require the conditions $C_1$ and $C_2$ to become "simultaneously" satisfied for collection to commence, taking into account the propagation delay $T_1$ between the UV-absorption detector 122 and the radiation detector 124. Additionally, the start and stop times are further delayed in accordance with the propagation time $T_2$ through the tube 134. If desired, a single purification run may comprise multiple collection periods, each having corresponding collection start and stop criteria and times.

In a very simple implementation, the criteria $C_1$ and $C_2$ may be defined in terms of threshold values. For example, the UV-absorption criterion $C_1$ may be "true" whenever the UV-absorption or transmission falls below, or rises above, a specified trigger level, or equivalently whenever the detected UV photocurrent or voltage rises above a corresponding threshold level. A similar threshold might be defined comprising the criteria $C_2$ in relation to the radioactivity detector 124. Additional refinements may include filtering, or performing a running average, of the detected signals, in order to reduce noise, and avoid repetitive switching and/or false triggering. Alternatively, or additionally, a degree of hysteresis may be built into the criteria, such that the "turn on" threshold is set higher than the "turn off" threshold, in order to further reduce false triggering and/or repetitive switching, due to system noise.

As another option, operator input may be utilized to determine the criteria $C_1$ and $C_2$. For example, the operator may observe the detected UV-absorption data and radioactivity data in real time, for example via a graphical display, and manually indicate when appropriate detected levels have been reached, using the user interface devices 214. The computer 202 may then automatically account for the eluent propagation times, avoiding the need for the user to mentally "align" the data from the two detectors, and determine when to open and close the collection valve 126. In another implementation of this type, the computer 202 may adjust and "synchronise" (ie delay) the display of data received from the detectors 122, 124, so that displayed waveforms correspond with "notional" detected signals that would be measured at the collection valve 126, so that the user may operate the valve 126 manually while directly observing the displayed waveforms.

In accordance with a further variation, delays within the tubes 132, 134 may be sufficiently large that they substantially exceed the period of time for which the pure radiopharmaceutical compound is available for collection (ie the time period for which the collection valve 126 will be open). In this case, completed data regarding the UV-absorption and the radioactivity of the portion of the eluent containing the desired radiopharmaceutical product will be available to the computer 202 before the compound has arrived at the collection valve 126 (ie prior to $T_{start}$). In this case, the computer 202 is able to perform a detailed analysis of the captured detector data over the relevant period of time in order to determine an optimum period during which the collection valve 126 should be open. Such analysis may include, for example, identifying relevant peaks in the UV-absorption data and/or the radioactivity data, identifying corresponding periods around the peaks during which sufficiently pure radiopharmaceutical product is present in the eluent, calculating the corresponding values of $T_{start}$ and $T_{stop}$, and operating the collection valve 126 accordingly and/or directing an operator to do so via the interface devices 214. As will be appreciated, such processing may avoid the need to rely upon simplistic criteria, such as predetermined threshold levels, and may therefore enable greater yield of higher purity product to be collected, with a high level of repeatability, and a reduced incidence of human error.

In view of the foregoing technical details, FIGS. 5 to 8 show exemplary screen shots illustrating a user interface in accordance with the presently preferred embodiment of the invention.

Figure 5:
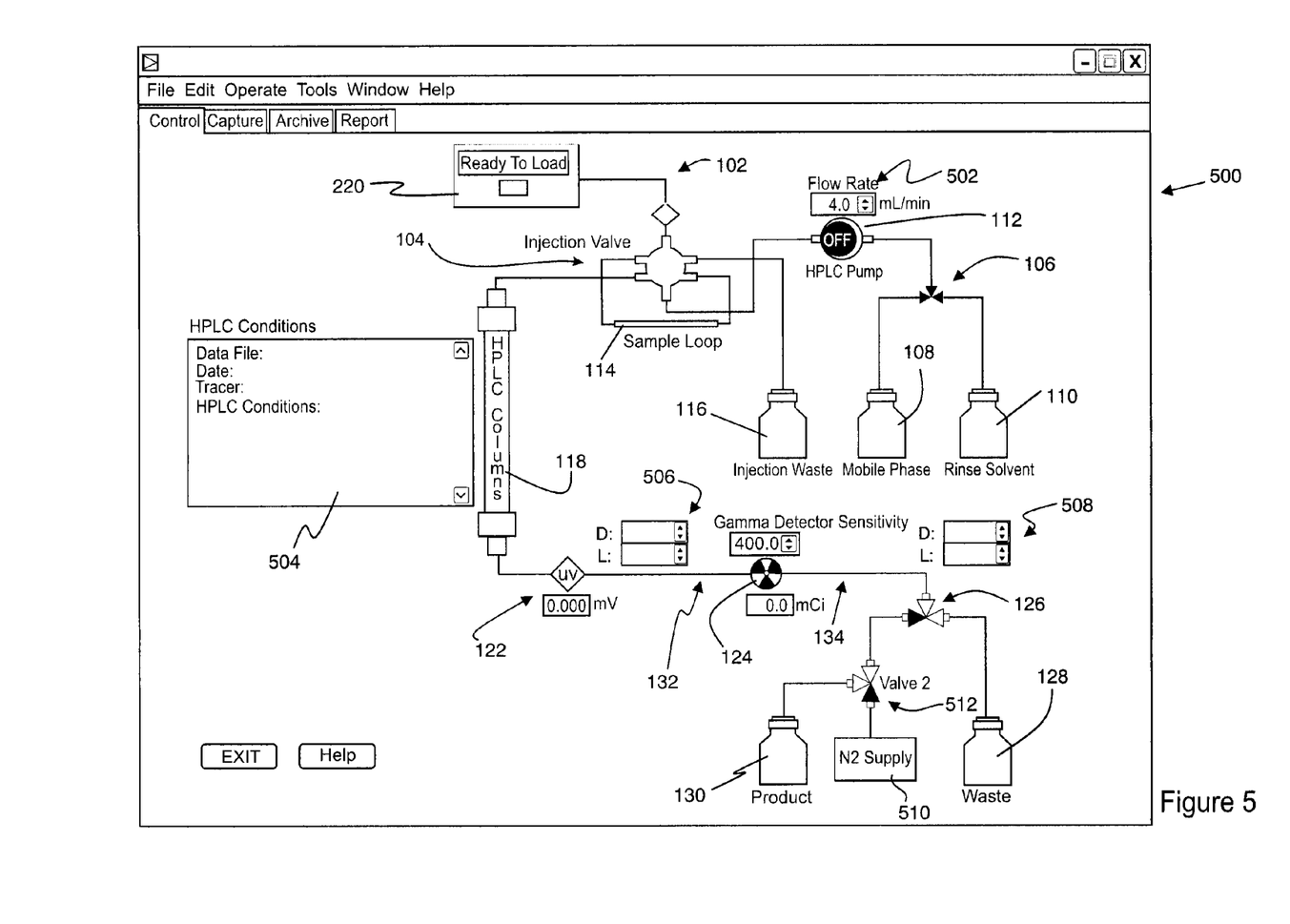
FIG. 5 shows a control screen of the user interface.

In particular, FIG. 5 shows a control screen 500, in which a schematic diagram of the system 100 is depicted. For convenience, reference numerals in FIG. 5 correspond as appropriate, with those utilized in the system 100 depicted in FIG. 1, in order to avoid duplication of corresponding description.

The operator is able to use the control screen 500 in order to observe the operation of the system 100, and to set relevant system parameters, as well as entering other pertinent information. The flow rate of the pump 112 is displayed in the text box 502. In the preferred embodiment, this value is entered by the operator to correspond with the actual flow rate of the pump utilized within the system. In alternative embodiments, this text entry box 502 may be used to set the pump flow rate, for example where the pump 112 is of a type that is able to be controlled in this manner via the control interface card 218. In still further embodiments, the computer 202 may be able to read a current pump flow rate setting from the device via the control card 218, and the displayed flow rate value may therefore be automatically obtained from the current pump configuration.

A text entry box 504 is provided, within which the user may enter any information related to the current purification process. This information is subsequently saved in a file, along with other data acquired in the course of purification.

The lengths and/or diameters of the lengths of tubing 132, 134 may be conveniently entered by the operator using the text boxes 506, 508.

In the system under control by the computer corresponding with the display 500, there is additionally included a nitrogen supply source 510, and a corresponding valve 512, enabling the tubes feeding the connection container 130 to be evacuated with the inert gas once collection is complete.

Figure 6:
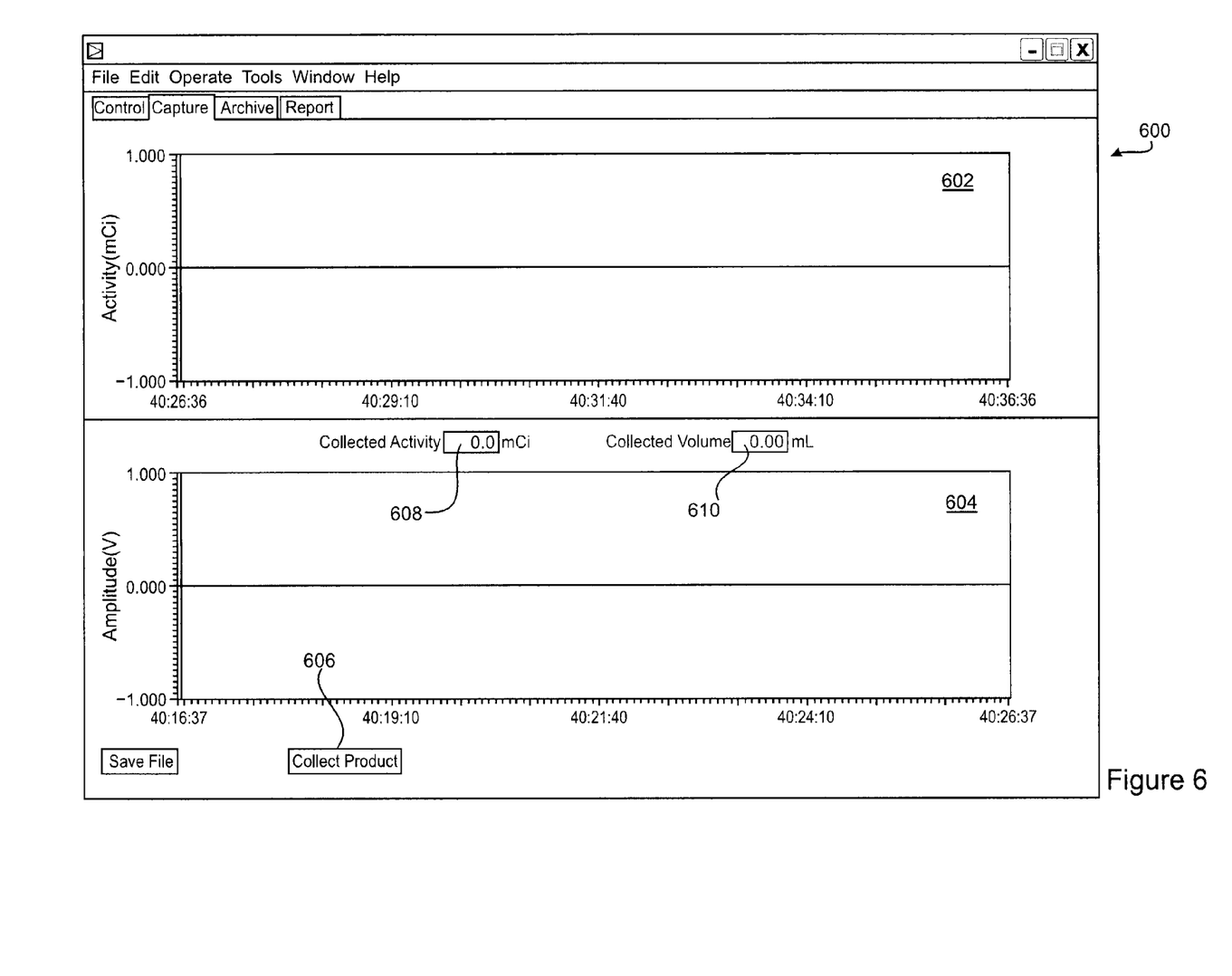
FIG. 6 shows a capture screen of the user interface.

FIG. 6 shows a capture screen 600, in which graphs of detected radioactivity 602 and UV-photovoltage amplitude 604 are displayed. The graphs 602, 604 are updated under control of the computer 202, and in real time, to enable the operator to observe the radioactivity and UV-absorption data during the process of purification. In the embodiment depicted, collection of the products (by opening valve 126) is performed under user control, and is initiated by operation of the "Collect Product" button 606. Additional information provided to the operator in the capture screen 600 includes a running total of collected activity 608, and collected volume 610.

Figure 7:
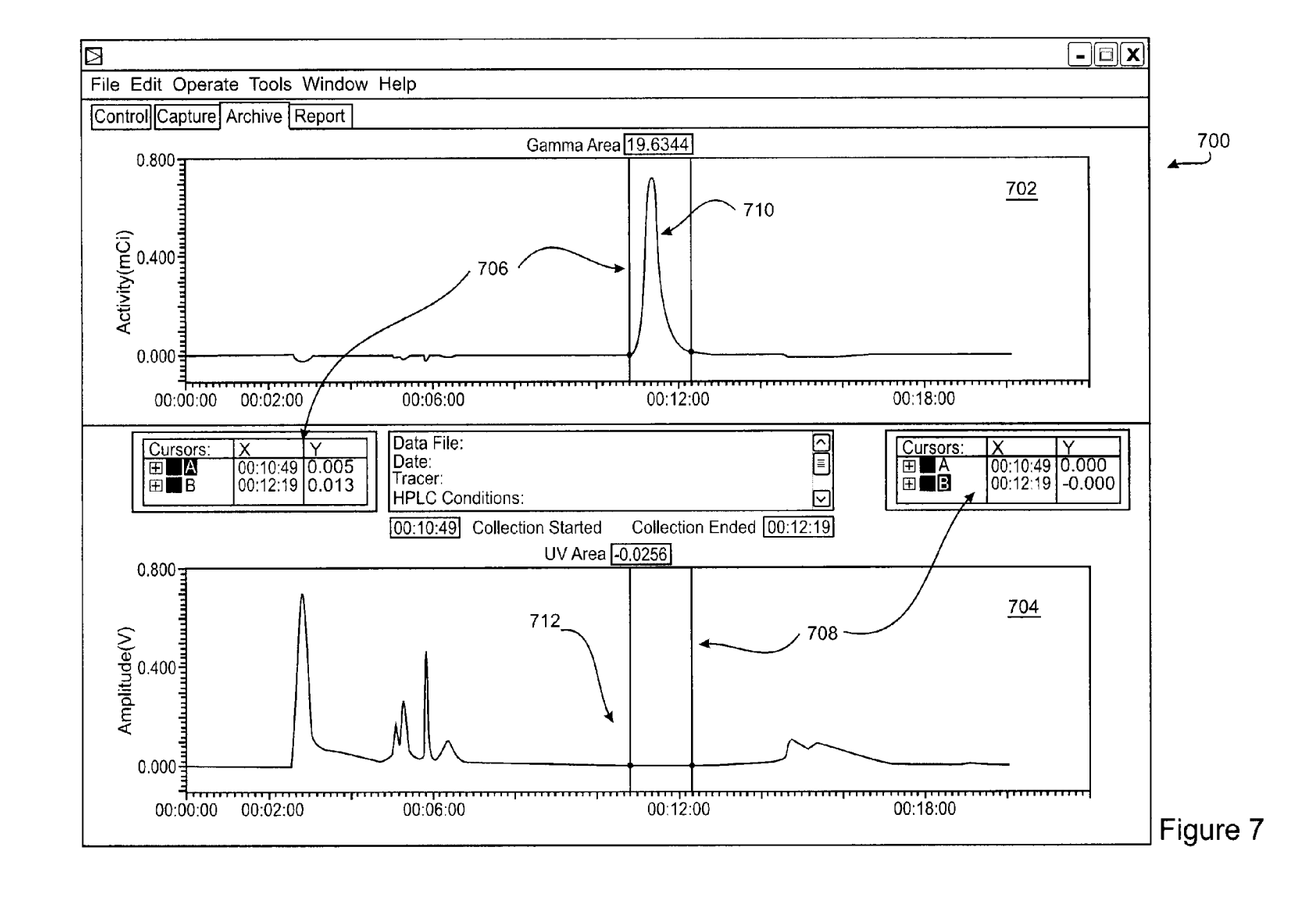
FIG. 7 shows an archive screen of the user interface.

FIG. 7 shows an archive screen 700 of the user interface. The archive screen is used to display previously acquired data. Such previously acquired information may be useful in assisting the operator to predict the expected product retention times during a subsequent synthesis and purification process of the same radiopharmaceutical compound. The screen 700 includes the previously recorded graphs of radioactivity 702 and UV-photovoltage amplitude 704. The time period during which collection was performed in the purification run is automatically indicated by the vertical cursors 706, 708. As can be seen, the desired product has been collected during a time period during which a radioactivity peak 710 is observed, and while simultaneously the detected UV-photovoltage amplitude is low.

Figure 8:
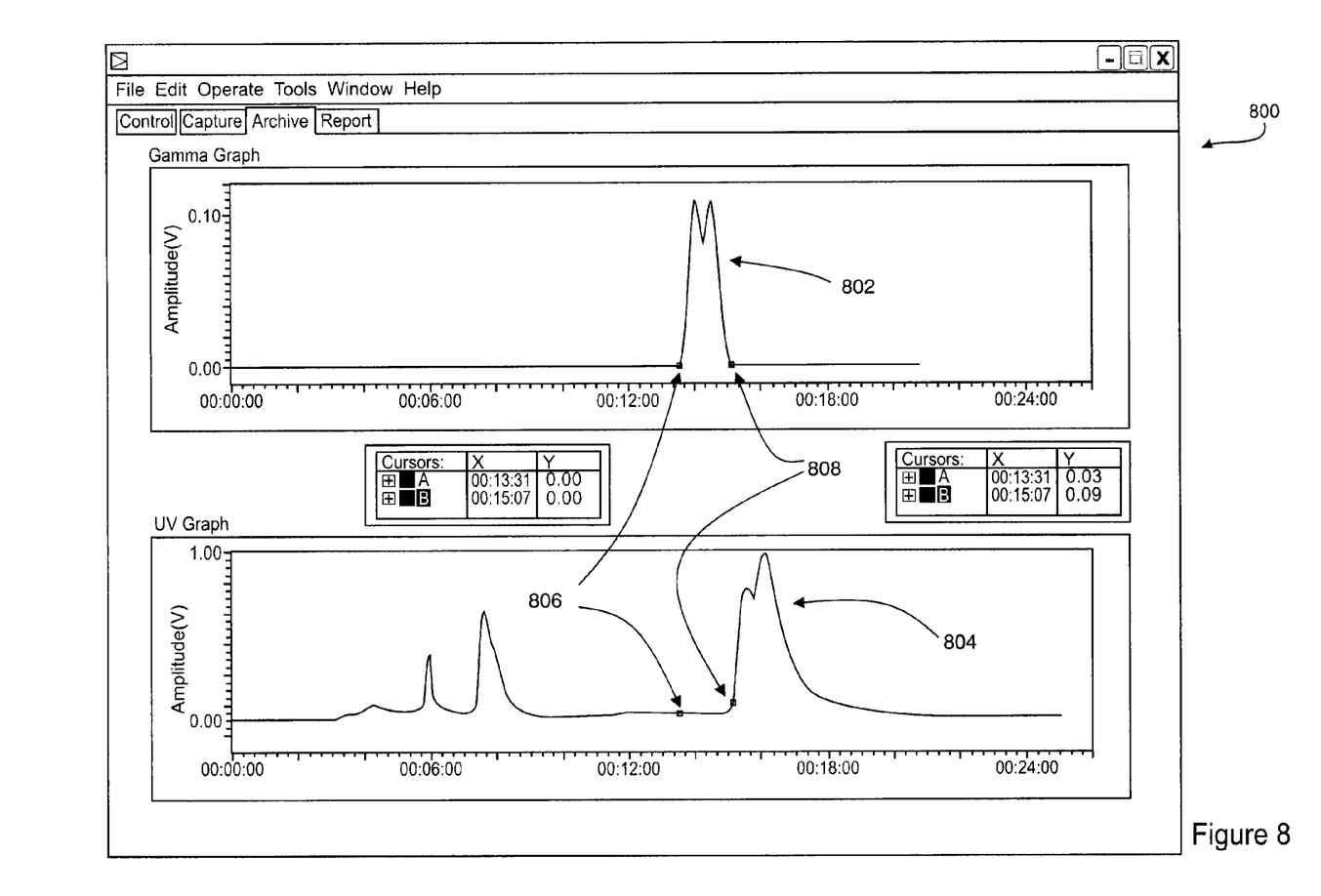
FIG. 8 shows a further archive screen of the user interface.

FIG. 8 shows a further archive screen 800 of the user interface, including previously acquired data illustrating the potential challenges of determining the most appropriate collection time period. In the purification process represented by the data in the archive screen 800, the radioactivity detector 124 precedes the UV-absorption detector 122. A peak 802, representing the presence of a high concentration of the desired product at the radioactivity detector, precedes a peak 804 in UV-transmission, representing the presence of an undesired impurity in the eluent immediately following the desired product. The nominal collection period, observed at the radioactivity detector 124, is indicated by the cursors A and B (806, 808), however this must be correctly referred to the collection valve location, taking into account the eluent propagation delays between the radioactivity detector 124 and the UV-absorption detector 122 (eg 8 seconds), and between the UV-absorption detector 122 and the collection valve 126 (eg 4 seconds). Due to the very close proximity within the eluent of the desired product and the impurity, failure to properly account for these delays may result in either contamination of the product, or reduced yield. In particular, accounting for the delay between the radioactivity detector 124 and the UV-absorption detector 122, there is an overlap between the radioactivity peak 802 and the UV-transmission peak 804 that is greater than is apparent in the data shown in the archive screen 800. It would accordingly be very difficult for an unaided human operator to collect the radiopharmaceutical product reliably and efficiently in this case. However, in accordance with an embodiment of the present invention, reliable and repeatable collection is facilitated.

Figure 9:
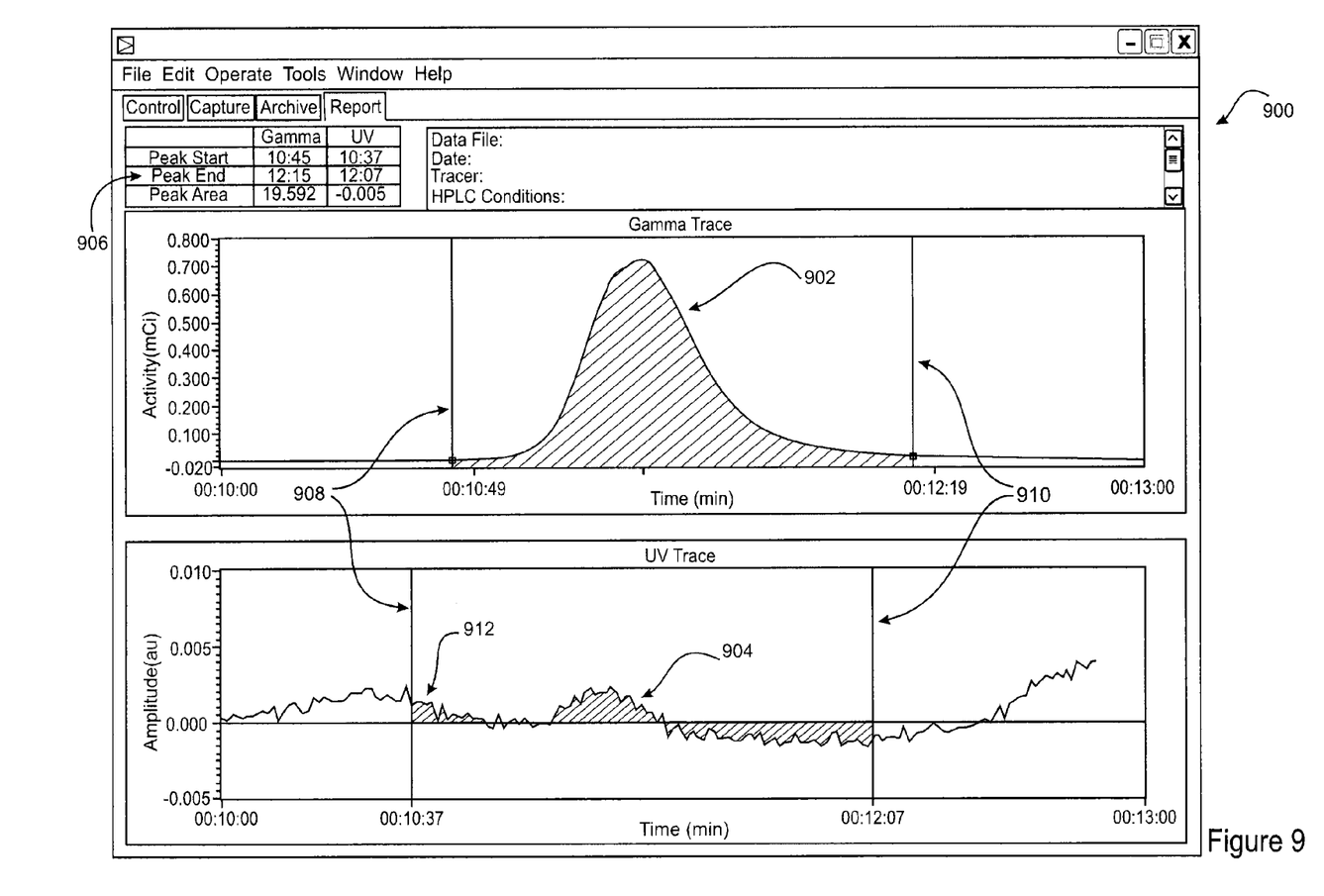
FIG. 9 shows a report screen of the user interface.

Finally, FIG. 9 shows a report screen 900 of the user interface. Notably, the report screen 900 corresponds with the production and purification of a different type of radiopharmaceutical tracer from that represented in the archive screen 800, and accordingly the UV-photovoltage trace is quite different in form. The report screen 900 provides a summary of the most recent purification results for future reference. In particular, the summary includes graphical representations of the radioactivity and UV-photovoltage amplitude traces, in which the relevant peaks 902, 904 have been highlighted. A peak summary table 906 is displayed in the top left hand corner of the screen 900. The vertical cursors 908 and 910 in the radioactivity and UV graphs may be manipulated by the operator to identify the desired peak periods, which are subsequently shaded as shown. The table 906 summarizes the specified cursor settings, and the computed areas under the enclosed curves. The operator is able to zoom in on selected portions of the display, and to adjust and align the graphs, in order to facilitate review and analysis of the purification results, which may be useful for improving the performance of future purification runs.

In the particular example shown in FIG. 9, the observed radioactivity peak extends from 10 minutes and 45 seconds into the purification run, until 12 minutes and 15 seconds. In the purification setup, the UV detector 122 precedes the radioactivity detector 124, and the corresponding period in the UV-photovoltage amplitude trace extends from 10 minutes and 37 seconds to 12 minutes and seven seconds. Collection was performed in this example between 10 minutes and 49 seconds and 12 minutes and 19 seconds. This collection period encompasses the main portion of the radioactivity peak 902, as well as the UV transmission peak 904 which is known to correspond with the desired product.

It is not clear, however, whether the UV transmission peak 912 which precedes the product peak 904, represents an unacceptable impurity presence. Taking into account the delays between the UV detector 122, the radioactivity detector 124, and the collection valve 126, it is apparent that a portion of the eluent corresponding with the peak 912 has been collected in this case. Typically, an objective of 98% purity of the collected product is established. Operation of the system 100 in accordance with an embodiment of the present invention, based upon analysis of relevant prior purification runs such as that shown in the report screen 900 in order to define appropriate collection criteria $C_1$ and $C_2$, is desirable to achieve reliable and repeatable purification satisfying specified purity objectives. Criteria may readily be established, for example, which would exclude all of the eluent corresponding with the peak 912 from collection.

While the foregoing description has covered various exemplary features of a preferred embodiment of the invention, it will be appreciated that this is not intended to be exhaustive of all possible functions provided within various embodiments of the invention. It will be understood that many variations of the present invention are possible, and the overall scope of the invention is as defined in the claims appended hereto.

I claim:

1. A method for use in an apparatus for purifying the product of a reaction to synthesise a radiopharmaceutical compound, wherein the apparatus includes a chromatography separating device, a UV-absorption detector located at a UV-monitoring location, a radioactivity detector located at a radioactivity monitoring location, and a collection container having a collection inlet valve located at a collection location, the method comprising:
   determining a first eluent propagation time between the UV-monitoring location and the radiation-monitoring location;
   determining a second eluent propagation time from at least one of the UV-monitoring location and the radioactivity-monitoring location to the collection location;
   passing the synthesis product through the chromatographic separating device to produce a corresponding eluent;

monitoring UV-absorption of the eluent to identify a first time period in which a substantially pure sample of the radiopharmaceutical compound is present at the UV-monitoring location;

monitoring radioactivity of the eluent to identify a second time period in which a substantially high concentration of the radiopharmaceutical compound is present at the radioactivity-monitoring location;

determining a third time period in which a substantially pure sample of the radiopharmaceutical compound is present at the collection location in a substantially high concentration, based upon said first time period, said second time period, said first eluent-propagation delay, and said second eluent-propagation delay; and opening the collection inlet valve during the third time period to collect the purified radiopharmaceutical compound in the collection container.

2. The method of claim 1 wherein the first and second eluent propagation times are determined based upon a flow rate of eluent and interior diameters and lengths of tubing connecting the UV-absorption detector, the radioactivity detector, and the collection inlet valve.

3. The method of claim 1 wherein the first time period and the second time period are identified based upon predetermined criteria of UV-absorption and radioactivity measured at the UV-absorption detector and the radioactivity detector respectively.

4. The method of claim 3 wherein the predetermined criteria comprise thresholds of detected UV-radiation and detected radioactivity.

5. The method of claim 3 wherein the predetermined criteria comprise criteria obtained by analysis of measured peaks in UV-absorption and radioactivity.

6. The method of claim 3 wherein the third time period is determined based upon simultaneous satisfaction of the UV-absorption criterion and the radioactivity criterion at the collection location.

7. An apparatus for purifying the product of a reaction to synthesise a radiopharmaceutical compound, wherein the apparatus includes a chromatographic separating device, a UV-absorption detector located at a UV-monitoring location, a radioactivity detector located at a radioactivity monitoring location, and a collection container having a collection inlet valve located at a collection location, the apparatus further comprising:

means for determining a first eluent propagation time between the UV-monitoring location and the radiation-monitoring location;

means for determining a second eluent propagation time from at least one of the UV-monitoring location and the radiation-monitoring location to the collection location;

means for monitoring the UV-absorption of the eluent to identify a first time period in which a substantially pure sample of the radiopharmaceutical compound is present at the UV-monitoring and location;

means for monitoring radioactivity of the eluent to identify a second time period in which a substantially high concentration of the radiopharmaceutical compound is present at the radioactivity-monitoring location;

means for determining a third time period in which a substantially pure sample of the radiopharmaceutical compound is present at the collection location in a substantially high concentration, based upon said first time period, said second time period, and said first eluent-propagation delay, and said second eluent-propagation delay; and means for opening the collection inlet valve during the third time period to collect the purified radiopharmaceutical compound in the collection container.

8. An apparatus for purifying the product of a reaction to synthesise a radiopharmaceutical compound, comprising:

a chromatographic separating device;

a UV-absorption detector located at a UV-monitoring location;

a radioactivity detector located at a radioactivity-monitoring location;

a collection container having a collection inlet valve located at a collection location;

at least one microprocessor;

at least one memory device operatively associated with the microprocessor; and at least one peripheral interface operatively associated with the microprocessor and enabling the microprocessor to receive UV-absorption data from the UV-absorption detector and radioactivity data from the radioactivity detector, wherein the memory device comprises computer executable instruction code stored therein which, when executed by the microprocessor, causes the microprocessor to:

determine a first eluent-propagation time between the UV-monitoring location and the radiation-monitoring location;

determine a second eluent-propagation time from at least one of the UV-monitoring location and the radiation-monitoring location to the collection location;

receive UV-absorption data from the UV-absorption detector in order to identify a first time period in which a sample of the radiopharmaceutical compound is present at the UV-monitoring location;

receive radioactivity data from the radioactivity detector so as to identify a second time period in which a substantially high concentration of the radiopharmaceutical compound is present at the radioactivity-monitoring location;

determine a third time period in which a substantially pure sample of the radiopharmaceutical compound is present at the collection location in a substantially high concentration, based upon said first time period, said second time period, said first eluent-propagation delay, and said second eluent-propagation delay; and generate an indication, during said third time period, that the collection inlet valve should be opened in order to collect the purified radiopharmaceutical compound in the collection container.

9. The apparatus of claim 8 wherein the peripheral interface comprises a data acquisition and control unit operatively interfaced with the UV-absorption detector and the radioactivity detector.

10. The apparatus of claim 8 further including at least one peripheral interface operatively associated with the microprocessor and enabling the microprocessor to control the collection inlet valve, whereby the collection inlet valve is opened during the third time period under automated control, in response to the generated indication.

11. The apparatus of claim 8 further including a user interface display, and wherein a visual indication is generated on the display during the third time period, whereby an operator of the apparatus opens the collection inlet valve under manual control.

* * * * *